United States Patent [19]

Wampler et al.

[11] Patent Number: 4,846,152
[45] Date of Patent: Jul. 11, 1989

[54] SINGLE-STAGE AXIAL FLOW BLOOD PUMP

[75] Inventors: Richard K. Wampler; John W. Carriker, both of Gold River; Kenneth C. Butler; John C. Moise, both of Carmichael, all of Calif.

[73] Assignee: Nimbus Medical, Inc., Rancho Cordova, Calif.

[21] Appl. No.: 124,874

[22] Filed: Nov. 24, 1987

[51] Int. Cl.$^4$ .............................................. A61F 1/24
[52] U.S. Cl. ............................... 600/16; 128/DIG. 3; 604/151; 415/900; 415/143; 623/3
[58] Field of Search ................. 128/1 D, DIG. 3; 604/151, 264; 415/210, 175, 170 A, 198.1, 199.4, 199.6, DIG. 4; 623/3

[56] References Cited

U.S. PATENT DOCUMENTS 3,291,381 12/1960 Troller ........................... 415/212 A
4,166,310 9/1979 Rothe ........................... 415/199.4 X
4,625,712 12/1980 Wampler ........................ 128/1 D

*Primary Examiner*—Alan Cohan
*Attorney, Agent, or Firm*—Weissenberger & Peterson

[57] ABSTRACT

A miniature high-speed intravascular blood pump is formed as a single stage with two rows of rotor blades and a single row of stator blades within a tubular housing. The rotor's first row produces a mixed centrifugal and axial flow, while the rotor's second row produces a purely axial flow. The blades of the second row are shaped so as to produce a uniform blood flow along the trailing edges of the blades. For this purpose, the bases of the outer trailing edges of the second row blades have a negative propulsion angle. The pump has a purge-sealed hydrostatic bearing which is spring-loaded for minimum gap. The pump is driven by a cable encased in a dual-lumen, fluid-filled cable sheath formed of a coextrusion of a soft, blood-compatible outer layer and a stiff, abrasion-resistant inner layer. The cable sheath serves both as a purge fluid supply for the bearing, and as a means for flushing abraded debris away from the pump.

15 Claims, 3 Drawing Sheets

SINGLE-STAGE AXIAL FLOW BLOOD PUMP

FIELD OF THE INVENTION

This invention relates to blood pumps, and more specifically to a high-speed, miniature pump for intravascular use.

BACKGROUND OF THE INVENTION

U.S. Pat. No. 4,625,712 discloses a miniature multistage axial-flow blood pump which can be percutaneously inserted into an artery for emergency heart assist. The pump is driven by a cable from a motor outside the body and provides a continuous blood flow of several liters per minute at high operating speeds.

In the course of research aimed at providing higher flow rates and even higher operating speeds with minimal hemolysis and increased safety, it has been found that the multi-stage design of U.S. Pat. No. 4,625,712 was not fully satisfactory because of limitations imposed by the allowable amount of hemolysis. On the other hand, conventional design wisdom indicated that single stage pumps could not be used because of the limitations in pressure rise per stage inherent in axial flow pumps.

Also, a problem arose from the fact that blood-compatible materials for the cable sheath were not sufficiently abrasion-resistant to safely allow prolonged operation of the pump.

SUMMARY OF THE INVENTION

The present invention overcomes the multistage problems by providing a single two-row stage containing one row of blades in which there is some axial and some centrifugal blood flow, and a second row of blades in which the blood flow is purely axial. In the preferred embodiment, the rotor carries three blades in each row, as does the stator.

Also, the invention overcomes the abrasion problem by forming the cable sheath as a coextrusion forming a pair of concentric lumens. The outer wall of the sheath is formed of a blood-compatible material while the inner wall is formed of an abrasion-resistant, relatively stiff material. The outer lumen (which preferably, for structural reasons, consists of a plurality of longitudinal passages disposed generally concentrically around the inner lumen) serves as a conduit for supplying purge fluid to the purge-sealed bearings of the pump, while the inner lumen contains the drive cable and serves as a return conduit which flushes any abraded sheath particles away from the pump. This has the additional advantage of providing a non-thrombogenic cable sheath surface while making the cable sheath stiff enough to prevent the formation of kinks during insertion.

It is therefore the object of the invention to provide a short, non-hemolytic, high-speed intravascular blood pump by using a single-stage, two-row rotor in which one row creates mixed axial and centrifugal blood flow and the other creates purely axial blood flow.

It is another object of the invention to provide a cable sheath for the above-described pump which is blood-compatible, yet abrasion-resistant and flushable. It is a further object of the invention to accomplish the foregoing objectives of the cable sheath by forming the sheath from a coextrusion of a blood-compatible non-thrombogenic material and an abrasion-resistant material.

DESCRIPTION OF THE PREFERRED EMBODIMENT

1. Introduction

An intravascular blood pump must satisfy several unusual criteria: (1) it must be small in diameter so as to readily fit into a blood vessel; (2) it must be short so as to be able to follow sharp bends in the blood vessel; (3) it must have as few hemolysis-producing interfaces as possible; and (4) it must be inexpensive to manufacture because it has to be a disposable item.

The foregoing requirements point to the desirability of using a single-stage pump. Single-stage pumps have fewer rotor/stator transitions than multi-stage pumps and therefore cause less hemolysis, even though they have to be operated faster in order to produce the necessary head. Single-stage pumps are also shorter than equivalent multi-stage pumps, and single-stage pumps are significantly less expensive to manufacture.

The problem arises from the fact that conventional pump design techniques teach that it is not possible to obtain a sufficient pressure rise in a single stage without causing stalls and other operational problems in the critical and unforgiving environment of a high-speed axial flow pump.

The present invention rests on the discovery that (1) axial flow intravascular blood pumps can be operated at higher speeds than conventional blade tip speed hemolysis calculations would indicate, and that (2) a single stage can be used in blood pumps of the type shown in U.S. Pat. No. 4,625,712 if the rotor is formed as a two-row stage, one row producing a mixed flow which is partially axial and partially centrifugal, and the other row producing a pure axial flow without cavitation, stall, or significant hemolysis.

The single-stage rotor construction described herein has a very stable HQ curve, i.e. it can accommodate, without stability problems, a wide range of pressure rises. This is important in intravascular blood pumps because the human heartbeat causes continual pressure rise fluctuations between the inlet and outlet of the pump ranging anywhere from 100 mmHg to a negative value.

2. The mixed-flow row

Figure 1:
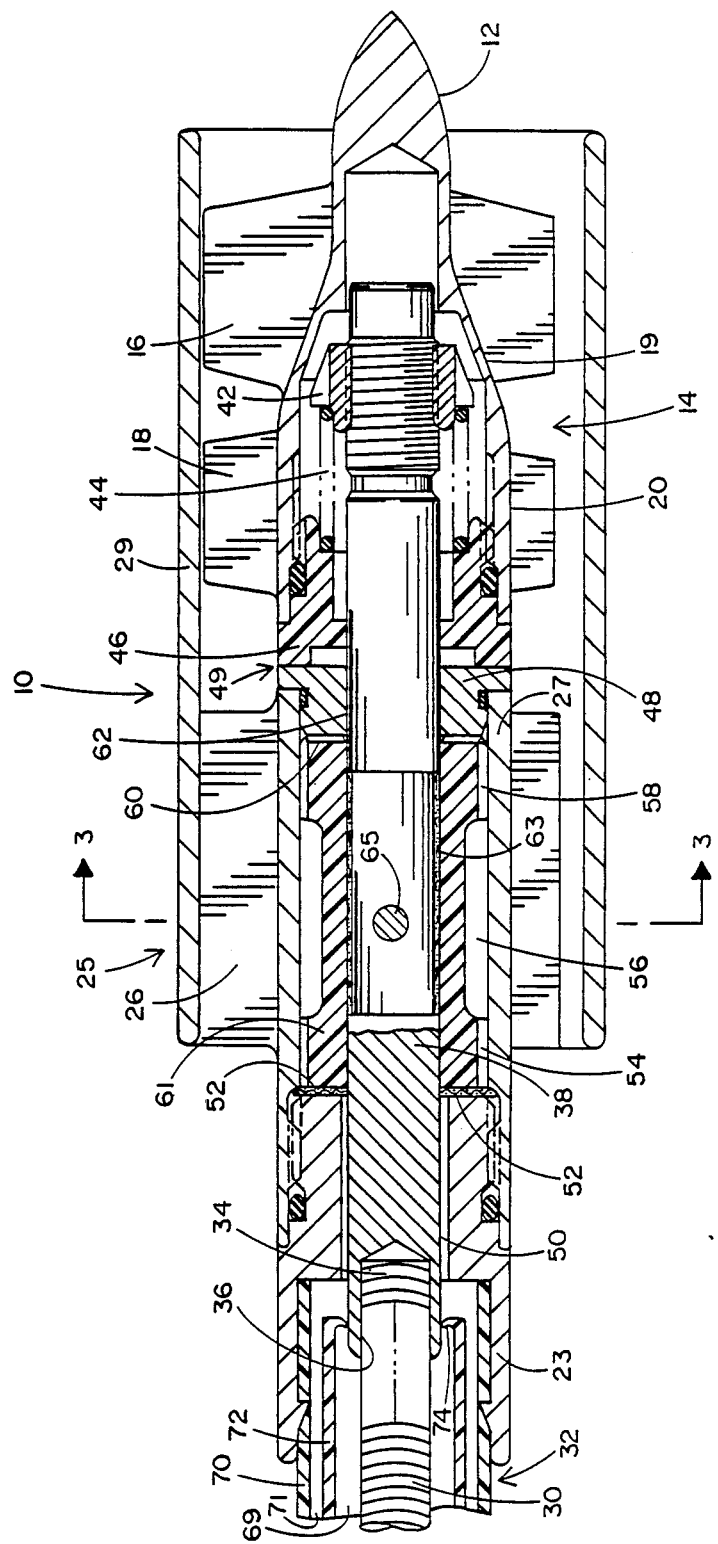
FIG. 1 is an axial section through the pump of this invention.

FIG. 1 shows the pump 10 of this invention in axial section. As a matter of size preference, the overall length of the pump 10 may be on the order of 1.5 cm, with an outside diameter on the order of 0.7 cm. The pump 10 may rotate at speeds on the order of 25,000 rpm and may produce a blood flow on the order of 3 l/min with a maximum pressure rise on the order of 100 mmHg.

Blood enters the pump 10 around the bullet-shaped hub 12 of the rotor 14 and within the outer housing 29. The hub 12 is provided with two rows of blades 16, 18. Each row in the preferred embodiment consists of three blades spaced 120 degrees apart, as it has been found that this blade arrangement unexpectedly optimizes the performance of the pump (conventional pump design would call for 5-10 blades per row) when combined with a three-blade stator. This is true because the three-blade arrangement has been found to provide the best compromise between flow guidance and drag loss.

Figure 2:
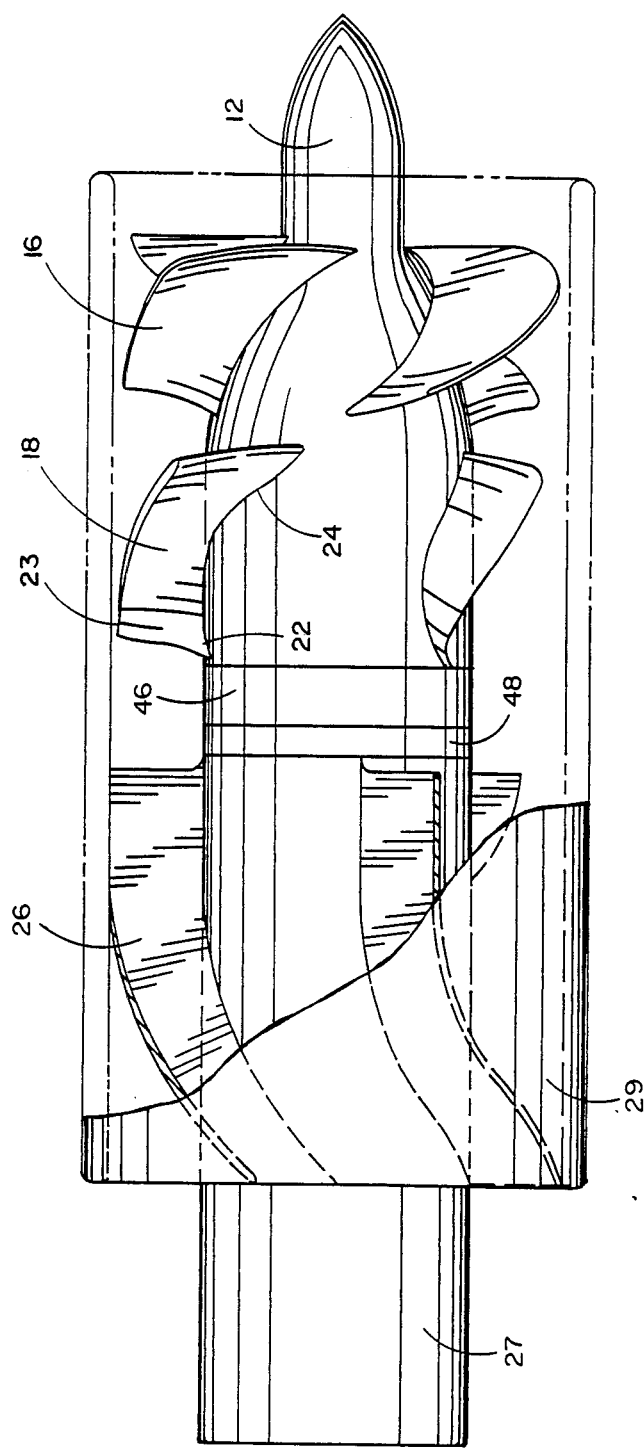
FIG. 2 is a partial side elevation, partly cut away, of the rotor and stator of the pump of FIG. 1.

In the area 19 of the first row of blades 16, the diameter of hub 12 increases in the direction of blood flow. This imparts to the blood an acceleration component in the radially outward direction, i.e. a centrifugal flow component. At the same time, the twist (FIG. 2) of the blades 16 produces an axial acceleration or flow component from right to left in FIG. 1. This mixed flow provides the additional pressure rise which makes it possible for the pump 10 to use a single-stage construction. The blades 16 of the mixed-flow row are so shaped, in accordance with conventional blade design criteria, as to maintain a uniform pressure rise through the row.

3. The axial flow row

The second row of rotor blades 18 (which, as mentioned above, preferably consists of three blades for optimum performance) lies on a constant-diameter portion 20 of hub 12, and therefore produces a purely axial flow. The twist (FIG. 2) of the blades 18 is designed to form a negative angle 22 at the base of the trailing edge adjacent the hub 12 but a positive angle 23 at the tip of the trailing edge away from the hub 12. The blades 18 also have a high leading edge twist 24. This arrangement maintains a uniform forward velocity of the blood flow along the trailing edge of each blade 18 in order to prevent any turbulence which might cause hemolysis or separation. It also provides an increased pressure rise necessary for enabling the stage to meet its operating criteria. The high twist is necessary to overcome the viscous losses in the low Reynolds range in which blood pumps of this size operate.

4. The stator

The stator 25 of the pump 10 includes a journal bearing 27, a cable sheath connector block 23, and the bearing block 48. It also contains, in the preferred embodiment, three reverse-twisted blades 26 which are substantially longer than blades 16 and 18, and in fact approach the overall length of the entire two-row rotor stage. The reverse twist and the unusual length of the stator blades 26 straightens and slows the blood flow so as to prevent (i.e. the deposit of blood particles.) It has been found that the elongation of the stator blades 26 also increases the efficiency of the pump 10. The stator blades 26 form the support for the housing 29.

5. Mechanical features The pump 10 is driven by a cable 30 which is rotatable within a cable sheath 32 extending from the outside of the patient's body to the pump 10 through the blood vessel into which the pump 10 is inserted. The tip 34 of cable 30 is fixed to the pump shaft 38 at 36.

A nut 42 threaded onto shaft 38 serves as a stop for the right end (in FIG. 1) of a spring 44. The left end of spring 44 bears against a plastic bearing block 46 assembled integrally with the rotor 14 so as to urge the block 46 and rotor 14 into engagement with the metal bearing block 48 of the stator and prevent rocking of the rotor 14. The interface between the bearing blocks 46 and 48 forms a hydrostatic thrust bearing 49 loaded for minimum gap by the pressure of spring 44.

The hub 12 is axially slidable on the shaft 38 but is rotated through the torque carrying ability of the spring 44. Using the spring for torque transmission minimizes axial sliding friction (which tends to interfere with the gap-minimizing function of spring 44) and allows uniform transmission of the axially directed spring force for seal loading.

Figure 4:
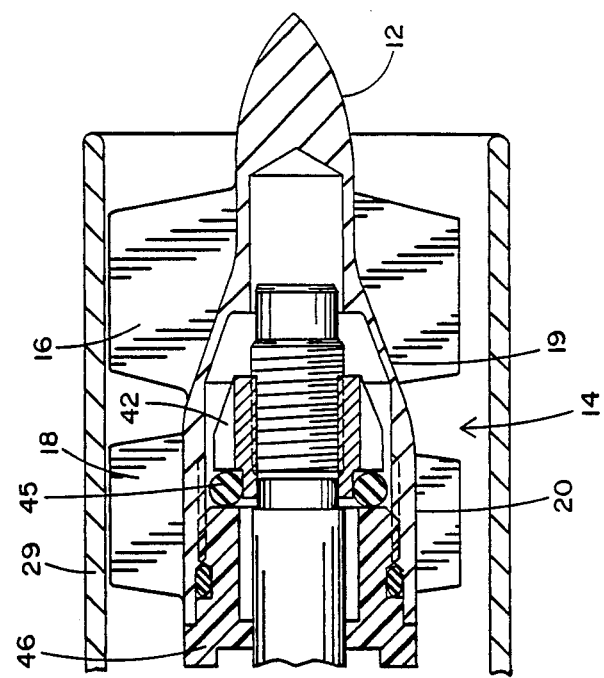
FIG. 4 is a partial axial section of an alternative embodiment of the pump of FIG. 1.
Figure 3:
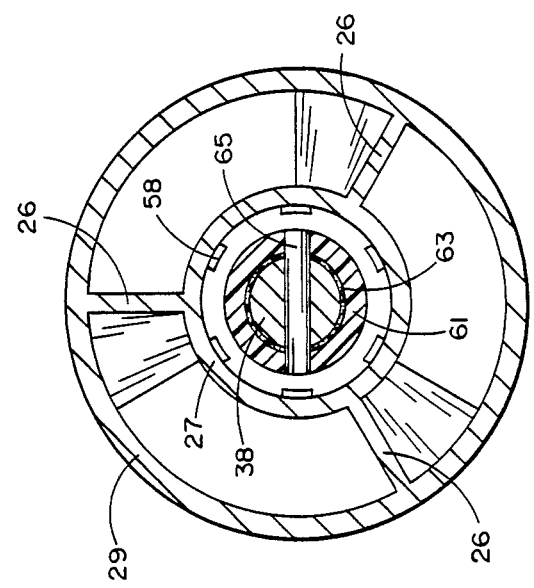
FIG. 3 is a transverse section along line 3—3 of FIG. 1.

FIG. 4 shows an alternate embodiment of the pump 10 in which a rubber O-ring 45 is used as the seal loading and torque transmitting means. Otherwise, the embodiment of FIG. 4 functions in the same manner as that of FIG. 1.

An external source shown in copending application Ser. No. 129,714 and entitled "Drive Mechanism For Powering Intravascular Blood Pumps" provides a blood-compatible purge fluid to the pump 10 at a substantially constant flow rate through the cable sheath 32. The load of the spring 44 (FIG. 1) or O-ring 45 (FIG. 4) is selected to maintain the pressure of the purge fluid at a level substantially higher than blood pressure. The purge fluid flows through passage 50, a particulate filter 52, and passages 54, 56, 58, 60 and 62 between the shaft 38 and the stator 25 to the bearing 49. The passages 54, 58 and 60 are formed in a plastic journal 61 which is preferably secured to the shaft 38 by an adhesive 63 and a pin 65. After serving as the bearing fluid in the hydrostatic bearing 49, the purge fluid exits radially outwardly into the blood stream.

It will be noted that the above-described construction exposes the bearing faces of bearing blocks 46, 48 for precision lapping when the rotor 14, shaft 38, connector block 23 and stator 25 are disassembled from each other. This and the simplicity of the single-stage design which permits easy investment casting of the rotor contributes to the low fabrication cost which is a distinct advantage in the field of disposable blood pumps.

6. The cable sheath

The cable sheath 32 serves both as a sheath for cable 30 and as the conduit for the purge fluid. This combination, however, presents a compatibility problem. In order to properly thread the pump 10 through the vascular system and prevent excessively sharp curves in the path of the cable 30, the cable sheath 32 must be quite stiff. In addition, it must be abrasion-resistant so that the cable 30 cannot rub through it during prolonged use. On the other hand, the outer surface of the cable sheath must be relatively soft to avoid damage to the blood vessel wall.

The invention solves this problem by using a preferably coextruded dual-lumen cable sheath forming an inner cylindrical lumen 69 and an outer lumen 71. For structural integrity, the outer lumen 71 is preferably formed as a plurality of separate, axially extending passages disposed generally concentrically around the inner lumen 69. The wall 70 of the outer lumen 71 is preferably formed of a relatively soft blood-compatible material, while the wall 72 of the inner lumen 69 is preferably formed of a stiff, abrasion-resistant material. A variety of suitable plastic materials having these qualities are known in the art. Purge fluid is conveyed to the pump 10 through the outer lumen 71. Some of the fluid enters the pump 10 at passage 50, while another portion of the fluid is sucked past the seal 74 by an appropriate apparatus such as that shown in the aforesaid copending application Ser. No. 129,714 filed Dec. 7, 1987 pending. The latter portion lubricates the cable 30 and flushes any cable sheath particles abrasively dislodged by cable 30 away from the pump 10.

What is claimed:

1. An intravascular blood pump, comprising:
(a) a substantially cylindrical stator; and
(b) a rotor having a hub and cooperating with said stator to pump blood axially through said pump, said stator and rotor defining an annular space therebetween;

(c) means including two rows of blades on said rotor, for maintaining a radially uniform forward velocity of said blood in said annular space at the trailing edge of said rotor blade means, one of said rows producing a mixed axial and centrifugal flow, and the other producing a substantially pure axial flow.

2. The blood pump of claim 1, in which the diameter of the hub of said rotor increases in the direction of flow along said one of said rows at a rate which, when taken together with the curvature of the blades of that row, produces a uniform pressure rise throughout the row.

3. The blood pump of claim 1, in which the shapes of the blades of said other of said rows is such as to produce a uniform flow velocity of said blood along the trailing edge of said blades.

4. The blood pump of claim 3, in which the base of the trailing end of said blades has a negative propulsion angle.

5. The blood pump of claim 1, in which said stator and each said row of blades has three blades.

6. An intravascular blood pump comprising:
(a) a substantially cylindrical stator; and
(b) a rotor cooperating with said stator to pump blood axially through said pump;
(c) said stator and rotor forming a single stage pump;
(d) said rotor having two rows of blades, one of said rows producing a mixed axial and centrifugal flow, and the other producing a substantially purely axial flow;
(e) cable means operatively connected to said rotor for driving the same; and
(f) a cable sheath secured to said pump in fluid-tight relationship, said cable means being disposed longitudinally within said cable sheath;
(g) said cable sheath including a pair of substantially parallel lumens.

7. The blood pump of claim 6, in which purge fluid is conveyed toward said pump through one of said lumens, said cable means being disposed in the other of said lumens, and in which a portion of the purge fluid is conveyed away from said pump through said other lumen to flush the same.

8. The blood pump of claim 6, in which said lumens are concentric, the outer wall of said outer lumen being formed of a substantially soft, blood-compatible material, and the wall of said inner lumen being formed of a substantially stiff, abrasion-resistant material.

9. The pump of claim 8, in which said lumen walls are coextruded.

10. An intravascular blood pump, comprising:
(a) a substantially cylindrical stator; and
(b) a rotor cooperating with said stator to pump blood axially through said pump;
(c) said stator and rotor forming a single stage pump;
(d) said rotor having two rows of blades, one of said rows producing a mixed axial and centrifugal flow, and the other producing a substantially purely axial flow;
(e) a purge-sealed hydrostatic bearing between said rotor and said stator disposed substantially transversely to the axis of said pump, and
(f) resilient means for biasing said rotor against said stator at said bearing.

11. The blood pump of claim 10, in which said resilient means is a spring.

12. The blood pump of claim 10, in which said resilient means is an O-ring.

13. The blood pump of claim 10, further comprising a drive shaft for driving said rotor, said resilient means being interposed between said drive shaft and said rotor so as to transmit to said rotor the driving torque of said drive shaft.

14. The blood pump of claim 13, in which said resilient means is a spring.

15. The blood pump of claim 13, in which said resilient means is an O-ring.

* * * * *